US00PP19628P2

(12) United States Plant Patent
Oudshoorn

(10) Patent No.: US PP19,628 P2
(45) Date of Patent: Jan. 20, 2009

(54) ***ERODIUM* PLANT NAMED 'FREEDOM'**

(50) Latin Name: *Erodium hybrida*
Varietal Denomination: Freedom

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/999,291

(22) Filed: Dec. 4, 2007

(51) Int. Cl.
*A01H 5/00* (2006.01)

(52) U.S. Cl. ..... Plt./263.1
(58) Field of Classification Search ..... Plt./263.1
See application file for complete search history.

*Primary Examiner*—Kent L Bell
(74) *Attorney, Agent, or Firm*—C. A. Whealy

(57) ABSTRACT

A new and distinct cultivar of *Erodium* plant named 'Freedom', characterized by its upright and outwardly spreading plant habit; strong growth habit; freely basal branching habit; dark green-colored leaves; freely flowering habit; large pink-colored flowers with dark purple-colored centers; and good garden performance.

3 Drawing Sheets

Botanical designation: *Erodium hybrida.*
Cultivar denomination: 'Freedom'.

BACKGROUND OF THE INVENTION

The present invention relates to a new and distinct cultivar of *Erodium*, botanically known as *Erodium hydrida*, and hereinafter referred to by the name 'Freedom'.

The new *Erodium* is a product of a planned breeding program conducted by the Inventor in Rijpwetering, The Netherlands. The objective of the breeding program is to create new strong and healthy *Erodium* cultivars with attractive flowers.

The new *Erodium* originated from an open-pollination in June, 2002, of the *Erodium hybrida* cultivar France Choice, not patented, as the female, or seed, parent with an unknown selection of *Erodium hybrida* as the male, or pollen, parent. The new *Erodium* was discovered and selected by the Inventor as a single flowering plant from within the progeny of the stated open-pollination grown in a controlled environment in Rijpwetering, The Netherlands in July, 2003.

Asexual reproduction of the new *Erodium* by divisions in a controlled environment in Rijpwetering, The Netherlands since March, 2004, has shown that the unique features of this new *Erodium* are stable and reproduced true to type in successive generations.

SUMMARY OF THE INVENTION

The cultivar Freedom has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Freedom'. These characteristics in combination distinguish 'Freedom' as a new and distinct cultivar of *Erodium*:

1. Upright and outwardly spreading plant habit.
2. Strong growth habit.

3. Freely basal branching habit.
4. Dark green-colored leaves.
5. Freely flowering habit.
6. Large pink-colored flowers with dark purple-colored centers.
7. Good garden performance.

Plants of the new *Erodium* differ primarily from plants of the female parent, the cultivar France Choice, in the following characteristics:

1. Plants of the new *Erodium* are stronger than plants of the cultivar France Choice.
2. Plants of the new *Erodium* have larger leaves than plants of the cultivar France Choice.
3. Plants of the new *Erodium* have larger flowers than plants of the cultivar France Choice.

Plants of the new *Erodium* can be compared to plants of the *Erodium hybrida* cultivar Charm, not patented. In side-by-side comparisons, plants of the new *Erodium* differed primarily from plants of the cultivar Charm in flower color as plants of the cultivar Charm had light pink-colored flowers. In addition, plants of the new *Erodium* and Charm differed in leaf shape as plants of the cultivar Charm had oakleaf-shaped leaves.

BRIEF DESCRIPTION OF THE PHOTOGRAPHS

The accompanying colored photographs illustrate the overall appearance of the new *Erodium*, showing the colors as true as it is reasonably possible to obtain in colored reproductions of this type. Colors in the photographs may differ slightly from the color values cited in the detailed botanical description which accurately describe the colors of the new *Erodium.*

The photograph on the first sheet comprises a side perspective view of typical flowering plant of 'Freedom' grown in an outdoor nursery.

The photograph on the second sheet is a close-up view of typical flowers and flower buds of 'Freedom'.

The photograph at the top of the third sheet is a close-up view of a typical leaf of 'Freedom'.

The photograph at the bottom of the third sheet is a close-up view of a typical developing fruit of 'Freedom'.

DETAILED BOTANICAL DESCRIPTION

The aforementioned photographs and following observations, measurements and values describe plants grown in Rijpwetering, The Netherlands in an outdoor nursery during the early autumn. During the production of the plants, day temperatures ranged from 12° C. to 28° C. night temperatures ranged from 4° C. to 14° C. and light levels ranged from 10,000 lux to 50,000 lux. Plants were about one year old when the photographs and the description were taken. In the detailed description, color references are made to The Royal Horticultural Society Colour Chart, 2001 Edition, except where general terms of ordinary dictionary significance are used.

Botanical classification: *Erodium hybrida* cultivar Freedom.

Parentage:

*Female, or seed, parent.*—*Erodium hybrida* cultivar France Choice, not patented.

*Male or pollen parent.*—Unknown selection of *Erodium hybrida*, not patented.

Propagation:

*Type.*—By divisions.

*Time to produce a rooted young plant, summer.*—About 20 weeks.

*Root description.*—Medium in thickness, moderately fibrous; 199B to 199D in color.

*Rooting habit.*—Sparse.

Plant description:

*General appearance.*—Herbaceous perennial. Upright and outwardly spreading plant habit; broad inverted triangle in shape.

*Growth and branching habit.*—Low vigor to moderately vigorous growth habit. Freely basal branching habit with about three basal rosettes developing per plant.

*Plant height, to top of umbels.*—About 26.3 cm.

*Plant width.*—About 26.2 cm.

*Basal rosettes.*—Height: About 8 mm. Diameter: About 4 mm. Internode length: About 1 mm. Stem texture: Smooth, glabrous. Stem strength: Strong. Color: 144C.

Foliage description:

*Arrangement.*—Basal; compound with nine leaflets per leaf.

*Length, leaves.*—About 5.3 cm.

*Length, leaflets.*—About 1.3 cm.

*Width, leaves.*—About 3.5 cm.

*Width, leaflets.*—About 1.1 cm.

*Shape, leaves and leaflets.*—Narrowly triangular.

*Apex, leaves and leaflets.*—Acute.

*Base, leaves and leaflets.*—Hastate.

*Margin, leaflets.*—Fringed.

*Venation pattern, leaflets.*—Pinnate.

*Texture, upper and lower surfaces, leaflets.*—Moderately pubescent.

*Color, leaflets.*—Developing foliage, upper surface: 143A. Developing foliage, lower surface: 143C. Fully developed, upper surface: 143A; venation, 143B. Fully developed, lower surface: Between 143C and 144A; venation, 144B.

*Petiole.*—Length: About 7.4 cm. Diameter: About 1.5 mm. Texture, upper and lower surfaces: Pubescent. Color, upper and lower surfaces: 144A.

Flower description:

*Flower arrangement.*—Single rotate flowers arranged in umbels arising from apical leaf axils. Flowers face upright to outward. Flowers not fragrant.

*Quantity of flowers.*—Freely flowering habit; about eight flowers develop per umbel.

*Flowering season.*—In The Netherlands, flowering is continuous from early summer to autumn. Flowers not persistent.

*Flower longevity.*—Flowers last about five days on the plant.

*Inflorescence height.*—About 6.3 cm.

*Inflorescence diameter.*—About 8.4 cm.

*Flower diameter.*—About 2.8 cm.

*Flower depth (height).*—About 1.1 cm.

*Flower buds.*—Length: About 8 mm. Diameter: About 4 mm. Shape: Obovate. Color: 143B to 143C; stripes, 143A.

*Petals.*—Quantity per flower: Five in a single whorl; two upper petals and three larger lower petals. Length, upper petals: About 1.5 cm. Length, lower petals: About 1.6 cm. Width, upper petals: About 1.3 cm. Width, lower petals: About 1.5 cm. Shape: Obcordate to rhomboidal. Apex: Rounded. Base: Attenuate. Margin: Entire. Texture, upper and lower surfaces: Smooth, glabrous. Color, upper petals: When opening and fully opened, upper surface: N80C to N80D; basal spot, N186A; venation, N80A to N80B. When opening and fully opened, lower surface: N80D; basal spot, N186A; venation, N80B. Color, lower petals: When opening and fully opened, upper surface: 76B; occasional basal spot, N186A; venation, 77A to 77B. When opening and fully opened, lower surface: 76B; occasional basal spot, N186A; venation, 77B to 77C.

*Sepals.*—Quantity per flower: Five, arranged in a single whorl. Length: About 1 cm. Width: About 3.5 mm. Shape: Oblong. Apex: Aristate. Base: Cuneate. Margin: Entire. Texture, upper surface: Smooth, glabrous; margins, sparsely pubescent. Texture, lower surface: Sparsely pubescent. Color: When opening and fully opened, upper surface: 144B; stripes, 143B. When opening and fully opened, lower surface: 144A; stripes, 146A.

*Peduncles.*—Length: About 19.6 cm. Diameter: About 2 mm. Strength: Moderately strong. Angle: About 40° C. from vertical. Color: 144A to 144B.

*Pedicels.*—Length: About 3.3 cm. Diameter: About 1 mm. Strength: Moderately strong. Angle: About 40° C. from vertical. Color: 144A to 144B.

*Reproductive organs.*—Androecium: Stamen quantity per flower: About five. Filament length: About 5 mm. Filament color: 77B. Anther length: About 2.5 mm. Anther shape: Oblong. Anther color: Lighter than 182D. Pollen amount: Scarce. Pollen color: Light greyed green. Gynoecium: Pistil quantity per flower: One. Pistil length: About 3.5 mm. Stigma shape: Five-parted; reflexed. Stigma color: 64A. Style length: About 2.5 mm. Style color: 178C to 178D. Ovary color: 143A to 143B.

*Fruits.*—Quantity per flower: One. Shape: Elongated and tapering like a heron's or stork's bill. Length: About 3.2 cm. Diameter: About 6 mm. Texture: Smooth, glabrous. Color: 151A.

*Seed*.—Length: About 4 mm. Diameter: About 2 mm. Color: 200A.

Disease/pest resistance: Plants of the new *Erodium* have not been observed to be resistant to pathogens and pests common to *Erodium*.

Garden performance: Plants of the new *Erodium* have exhibited good garden performance and to tolerate rain and wind and have been observed to be suitable for USDA Zone 5.

It is claimed:

1. A new and distinct *Erodium* plant named 'Freedom' as illustrated and described.

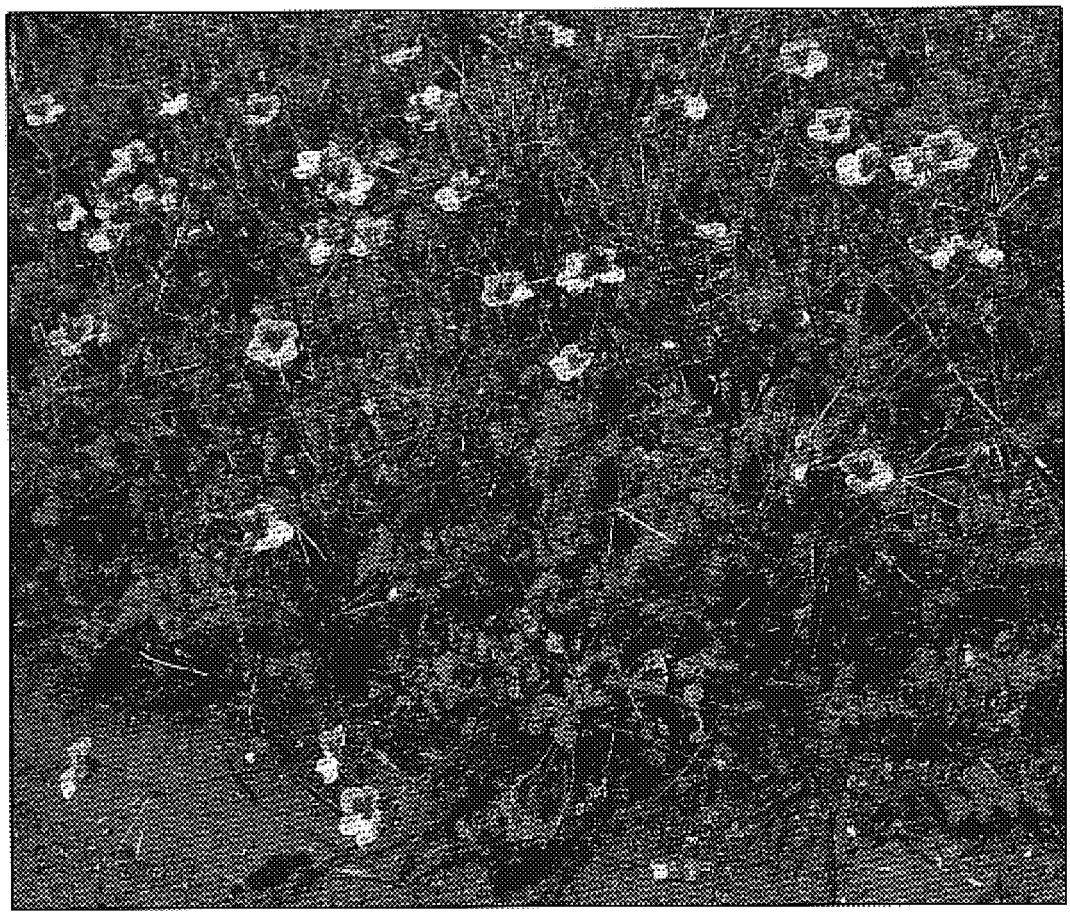

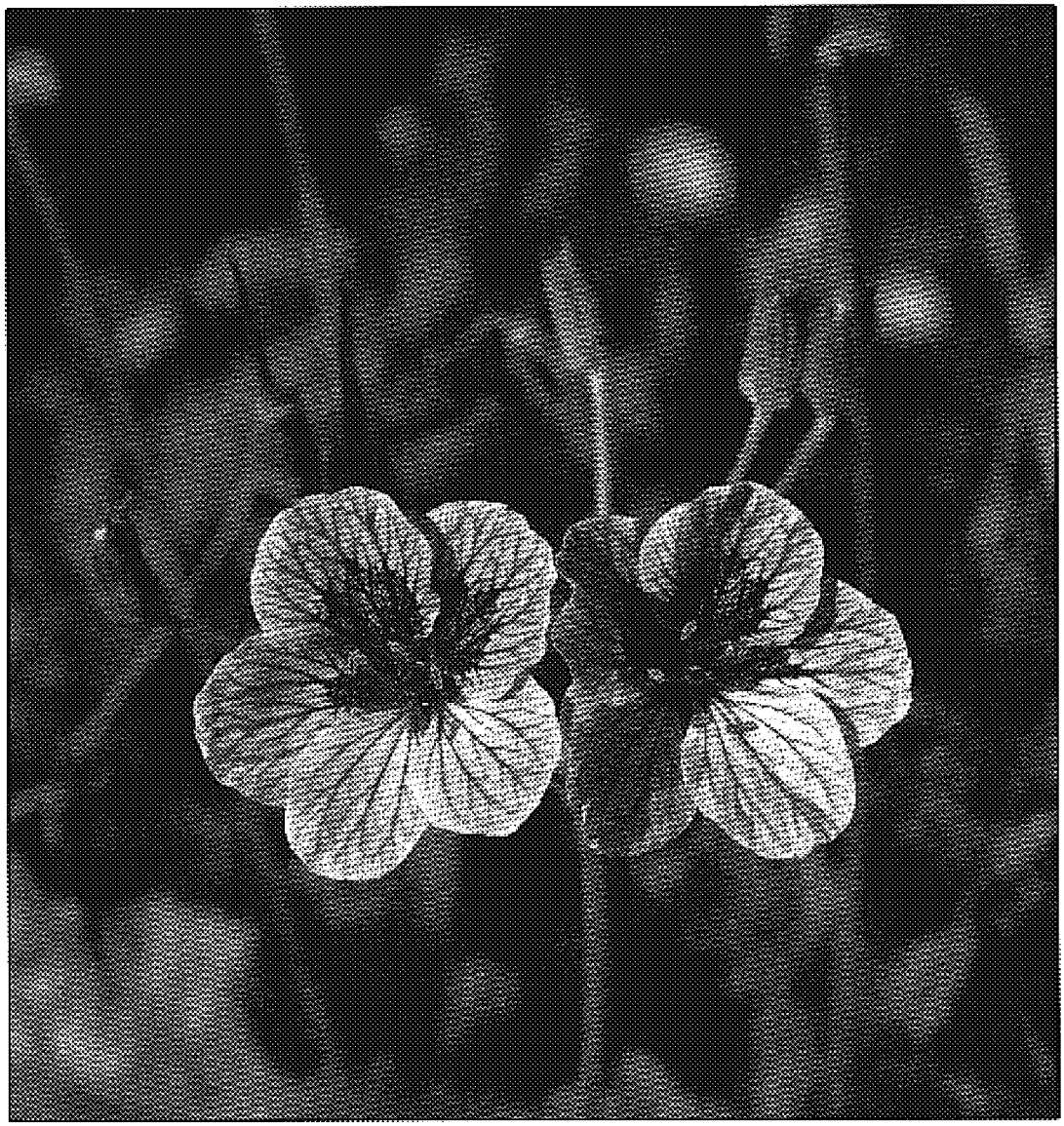

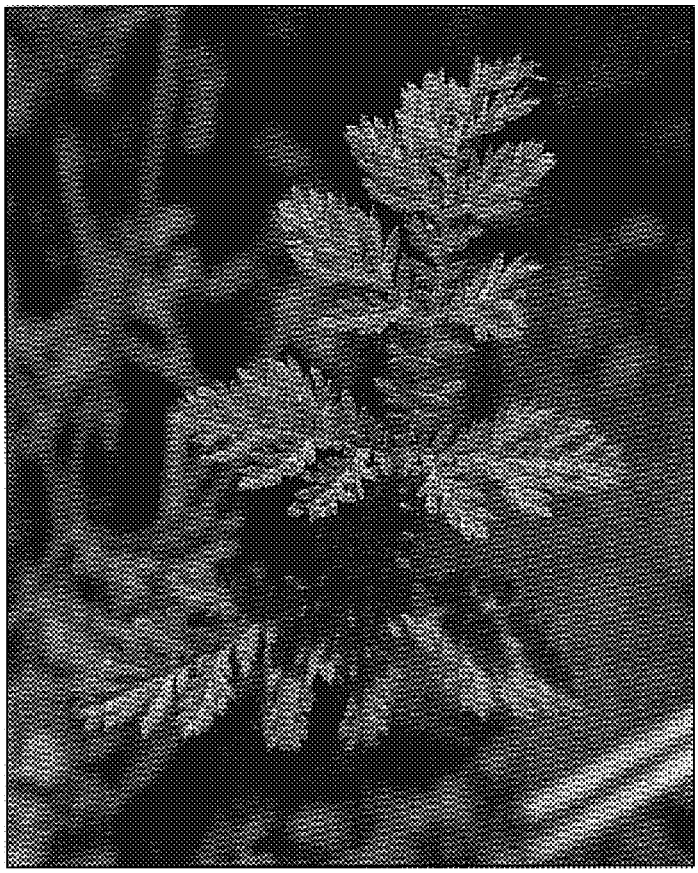
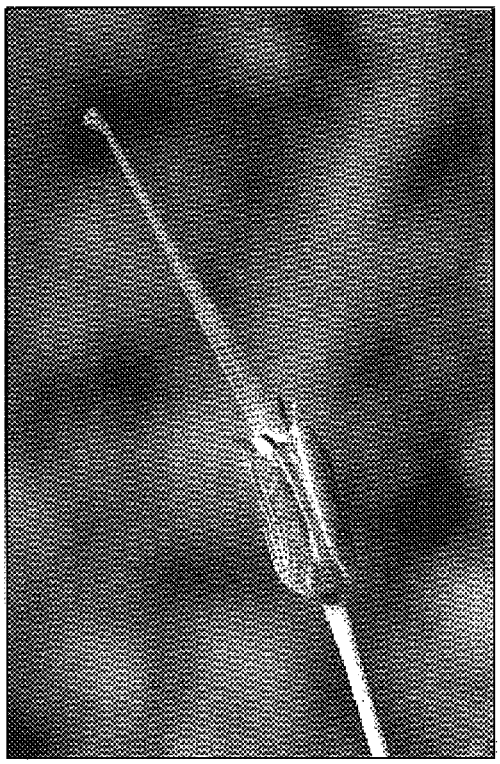

* * * * *